United States Patent [19]

Speranza et al.

[11] Patent Number: 5,103,056
[45] Date of Patent: Apr. 7, 1992

[54] AMIDOAMINES DERIVED FROM AMINES WITH AMINOPROPYL AND SECONDARY AMINE TERMINI

[75] Inventors: George P. Speranza, Austin; Donald H. Champion, Pflugerville, both of Tex.

[73] Assignee: Texaco Chemical Company, White Plains, N.Y.

[21] Appl. No.: 648,771

[22] Filed: Jan. 31, 1991

[51] Int. Cl.$^5$ ............................................. C07C 231/02
[52] U.S. Cl. .................................... 564/141; 564/138; 564/133; 564/151; 564/152; 564/153; 564/159; 564/160; 564/512; 549/429
[58] Field of Search ............... 564/141, 138, 512, 159, 564/160, 151, 152, 153; 549/429

[56] References Cited

U.S. PATENT DOCUMENTS 4,133,803  1/1979  Klein .................... 528/340

FOREIGN PATENT DOCUMENTS 6401278  8/1964  Netherlands .

OTHER PUBLICATIONS

Schloegl et al., Monatsh 95(3), 942–949 (1964) (abstract only CA 62:557g–558h).
Barefield et al., Inorg. Chem. 1976, 15(6), 1370-7 (abstract only CA 85: 13135c).
Gelbard et al., Bull. Soc. Chim. Fr. 1969, (4), 1191-70 (abstract only CA 71:49158n).

Primary Examiner—Glennon H. Hollrah
Assistant Examiner—S. Kumar
Attorney, Agent, or Firm—Jack H. Park; Kenneth R. Priem; Cynthia L. Kendrick

[57] ABSTRACT

Disclosed is a method for selective formation of amidoamines which comprises reacting a carboxylic acid group, such as, for example, a diacid or an aliphatic acid terminated amide with an aminopropylated disecondary amine which contains a secondary amine terminus in the same molecule at a temperature of about 150° C. to about 260°0 C.

8 Claims, No Drawings

AMIDOAMINES DERIVED FROM AMINES WITH AMINOPROPYL AND SECONDARY AMINE

BACKGROUND OF THE INVENTION

1. FIELD OF THE INVENTION

This invention relates to amidoamines. More particularly this invention relates to a method for increasing selectivity in the reaction between specified acid groups and multifunctional amines. Further, this invention relates to a novel method of preparing amidoamines by the selective reaction of, for example, aliphatic diacids with amines containing secondary amine termini.

2. DESCRIPTION

The addition of an acid group such as an aliphatic diacid or aliphatic acid terminated amide to primary amines to form amidoamines is known in the art, however obtaining the desired reaction is often difficult by virtue of the fact that a substantial amount of the amine reacts with the secondary amine, as well as the primary amine.

It does not appear that there have previously been any methods taught or suggested in the art for improving the selectivity of this type reaction. It would be very beneficial if such a method were available, since these primary amide products would be useful in the preparation of polyamidopolyureas and epoxy curing agents.

SUMMARY OF THE INVENTION

In accordance with the present invention it has been discovered that essentially 100% selectivity has been obtained in the preparation of amidoamines by reaction of aliphatic diacids with an aminopropyl group by employing an amine which also contains a secondary amine in the same molecule. The amidation reaction is conducted at moderate temperatures and does not require a catalyst.

DETAILED DESCRIPTION OF THE PREFERRED EMBODIMENT

According to the present invention there has been discovered a method for the selective formation of amidoamines which comprises reacting an acid group with an amine containing an aminopropyl group and a secondary amine terminus. The presence of the alkyl group on the secondary amine causes increased selectivity for the desired reaction at the primary amine. Thus the alkyl group essentially blocks reaction at the secondary amine. This can be contrasted with the less selective amidation of aminoethylpiperazine in which both the primary and secondary amines react.(See Example 2 for comparison.)

In particular, this invention comprises a method for reacting carboxylic acids and amines containing an aminopropyl group to produce amidoamine products which are useful in the preparation of polyamidopolyureas and epoxy curing agents. Products include, but are not limited to the following:

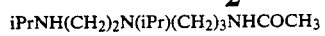  (1)

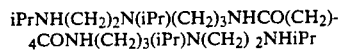  (2)

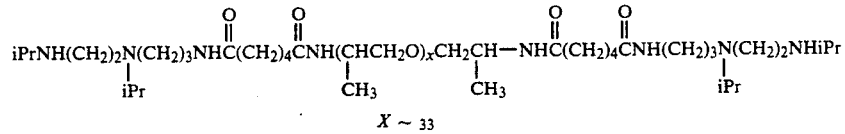  3)

$x \sim 33$

TERMINI

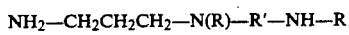  (4)

R = polyoxypropylene

The feedstock with which the acid group is reacted is a multifunctional amine. Preferably the feedstock is an aminopropyl disecondary amine of the formula:

$$NH_2-CH_2CH_2CH_2-N(R)-R'-NH-R$$

where R is a secondary or tertiary alkyl of 3-10 carbons and R' is ethylene or $(CH_2CH_2O)xCH_2CH_2$, where x is 1 to 3. Examples of suitable aminopropylated disecondary amines include N-(3-aminopropyl)-N,N'-di-t-butylethylenediamine(APDTBEDA), N-(3-aminopropyl)-N,N'-diisopropyltriethylene glycol diamine, N-(3-aminopropyl)-N,N'-di-sec-butyltriethylene glycol diamine and N-(3-aminopropyl)-N,N'-diisopropylethylenediamine(APDIPEDA). Preparation of these aminopropyl amines is given in copending U.S. Pat. application Ser. No. 07/568,927. The examples demonstrate, in particular, the amidation of N-(3-aminopropyl)-N,N'-diisopropylethylenediamine with various aliphatic diacids.

The acids which are useful in this invention include aliphatic diacids or aliphatic acid terminated amides prepared by the condensation of an excess amount of acid and a polyamine. Suitable aliphatic acids include carboxylic acids, such as, for example adipic, sebacic, azelaic, dodecanedioic and dimer acid. The examples demonstrate the effectiveness of adipic acid and acetic acid. In addition, acid terminated polyetheramides can be used. They are produced from dicarboxylic acids such as adipic, sebacic, azelaic or dodecanedioic acid and a polyether di- or triamine prepared, for example, by the procedure set forth in U.S. Pat. No. 4,239,635, or, alternatively, without the use of a solvent.

In some instances the use of an antioxidant is desirable to prevent degradation of the reactants or products during the condensation reaction. Suitable antioxidants include Irganox ® 1010, Irganox ® 1330, Irganox ® 1098 and Cyanox ® 2777. Irganox ® is the trademark for a series of high molecular weight stabilizers that inhibit oxidation and thermal degradation of many organic materials. They contain multifunctional chemical o groupings. Several are hindered polyphenols. Irganox ® is produced by the Ciba-Geigy Corporation. Cyanox ® is a tradename of American Cyanamide Company.

A desirable feature of this invention is that no catalyst is required for the amidation and the reaction takes place at moderate conditions. Temperatures of 150° C. to 300° C. are suitable and the preferred temperature is 170° to 250° C. In some instances a good method to use is to limit the temperature during the first part of the reaction to restrict the amount of aminopropyl compound removed with by-product water. The temperature is then intermittently increased to complete the reaction. (See example 4.)

The condensation reaction is conveniently carried out at atmospheric pressure but the reaction can also be done under vacuum (0.01 torr or more) or at slightly elevated pressures (to about 500 psig).

In the method of this invention the aminopropylated disecondary amines are added with an aliphatic diacid into a 250 ml flask equipped with a mechanical stirrer, thermometer, Dean-Stark trap and nitrogen inlets and outlets. The product is obtained from the reaction flask and by-product liquid is collected in the trap.

The present invention will be further illustrated by the following examples which are only for the purpose of illustration and are not to be regarded as limiting the invention in any way.

EXAMPLE 1

To a 100 ml flask equipped with a magnetic stirrer, thermometer and a Dean-Stark trap were charged 15g acetic acid and 51g N-(3-aminopropyl)-N,N$^1$-diisopropylethylenediamine (APDIPEDA). The mixture was heated to 225° C. as 4 ml water collected in the trap. When no more liquid collected, heating was continued for 1 hour. Analysis of the product by GC showed APDIPEDA, 97% of the primary amide and <1% of a heavier compound. NMR analysis of the primary amide showed it to consist entirely of

iPrNH(CH$_2$)$_2$(iPR)(CH$_2$)$_3$NHCOCH$_3$

EXAMPLE 2

The reaction described in Example 1 was repeated substituting 33g aminoethylpiperazine for the APDIPEDA. GC analysis of the product mixture showed the presence of a considerable amount of unreacted aminoethylpiperazine. NMR analysis revealed 65% of the primary amine groups reacted and 25% of the secondary amine groups reacted to form the following compounds:

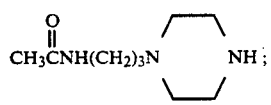

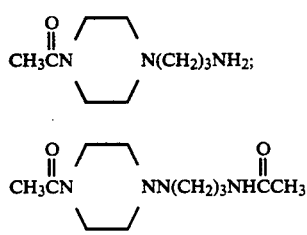

These two examples show the high selectivity for primary amide formation from APDIPEDA while aminoethylpiperazine is much less selective.

EXAMPLE 3

To a 250 ml flask equipped with a mechanical stirrer, thermometer, Dean-Stark trap and nitrogen inlet and outlets were added 50.3g (0.250 mol) APDIPEDA and 18.27g (0.125 mol) adipic acid. The mixture was heated with stirring to 220° C. for 105 min. as 7.8 ml of light material distilled into the trap. GC analysis showed it to contain some unreacted amine. The product was collected from the pot as a thick yellow liquid: acid number 14, 1.48 meq/g primary amine, 3.79 meq/g tertiary amine and 7.38 meq/g total amine. NMR data agreed with the following structure:

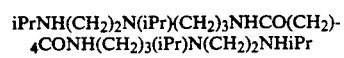

iPrNH(CH$_2$)$_2$N(iPr)(CH$_2$)$_3$NHCO(CH$_2$)$_4$CONH(CH$_2$)$_3$(iPr)N(CH$_2$)$_2$NHiPr

EXAMPLE 4

The reaction of Example 3 was repeated by heating 50.3g APDIPEDA, 18.27g adipic acid and 0.03g IRGANOX ® 245 antioxidant to about 185° C. for 45 min. then to about 200° C. for 30 min. During this time 7.2 ml of liquid collected in the trap. After cooling, the liquid and 1 ml water was returned to the reaction vessel. The reaction mixture was then heated at 180–184° C. for 2.4 hours, 196–199° C. for 1.2 hours and 222–223° C. for 1 hour as 2.4 ml liquid collected in the trap. The product was obtained as a thick yellow liquid from the reaction flask: acid number 8, 0.075 meq/g primary amine, 3.85 meq/g tertiary amine and 7.75 meq/g total amine. NMR analysis showed the sample to be nearly pure amidoamine with the structure given in Example 3.

EXAMPLE 5

To a 500 ml apparatus similar to the one described in Example 3 was charged 200g polyoxypropylene diamine with a molecular weight of 2000 (0.100 mol), 29.23g (0.200 mol) adipic acid and 0.13 CYANOX ®2777 antioxidant. The mixture was heated to 220° C. for 1.5 hours and cooled. After the addition of 40.27g (0.200 mol) APDIPEDA, heating was continued at 220 for 3 hours. The product was collected as 259g of yellow liquid: acid number 2, 0.070 meq/g primary amine, 0.77 meq/g tertiary amine and 1.51 meq/g total amine. These results are in good agreement (theory: 0,0,0.80 and 1.6 meq/g, respectively) for the formula shown.

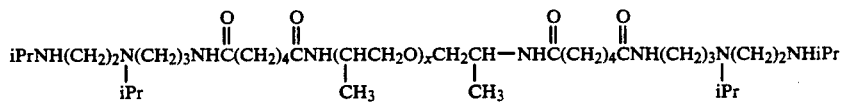

EXAMPLE 6

The reaction described in Example 5 was repeated with 200g (70.7 mmol) polyoxypropylene triamine of molecular weight approximately 3000, 31.0g (212 mmol) adipic acid and 0.14g CYANOX ® 2777 antioxidant. After heating to 220° C. for 1.5 hours the mixture was cooled to about 90° C. and 42.7g (212 mmol) APDIPEDA was added.

Heating was continued at 205–223° C. for about 2 hours to give the product as 263g of a yellow liquid: acid number 6, 0.16 meq/g primary amine, 0.704 meq/g tertiary amine and 1.48 meq/g total amine. A trifunctional secondary amine was formed analogous to the product described in Example 5.

EXAMPLE 7

The product from Example 4 (15.4g) and diglycidyl ether of bisphenol A (DGEBA) (11.5g) were heated to 50° C., mixed and poured into a 5 cm diameter weighing tin. The mixture was then cured at 50° C. for 6 hours and then at 100° C. for 1 hour to give a hard, clear orange disc.

EXAMPLE 8

The product from Example 6 (9.83g) and DESMOCAP® 11A (11.67g) were mixed and heated in a 50° C. oven for 2 hours and then at 100° C. for 30 min. to give a soft clear elastomer. DESMOCAP® 11A is a nonylphenol capped isocyanate prepolymer produced by Mobay.

EXAMPLE 9

To a 500 ml apparatus similar to Example 3 was charged 200g (0.1 mol.) polyoxypropylene diamine of molecular weight 2000, 29.2g of adipic acid (0.2 mols) and 0.13g CYANOX® 2777 antioxidant. The mixture was heated to about 220° C. for 1.5 hours. After cooling to 100° C., 45.9g (0.2 mols) of N-(3-aminopropyl)-N,N'-di-t-butylethylenediamine (APDTBEDA) was added and the mixture was heated to 190° C. for 1 hour and then to 220° C. for 2.5 hours. The product gave an amine assay of 1.44 meq/g, 1.48 meq/g being theoretical for

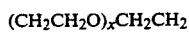

R = polyoxypropylene

What is claimed is:

1. A method for selective formation of amidoamines which comprises reacting an acid group selected from the group consisting of aliphatic carboxylic acid or an aliphatic acid terminated amide prepared by condensation of an excess amount of a dicarboxylic acid and a polyamine, with an amine containing a secondary terminus in the same molecule.

2. The method of claim 1 wherein the carboxylic acid is adipic acid.

3. The method of claim 1 where the polyamine is selected from the group consisting of polyoxypropylene diamine, polyoxyethylenediamine, polyoxyethylenepolyoxypropylene diamine and polytetrahydrofuran diamine.

4. The method of claim 1 wherein the reaction of a carboxylic acid with a primary amine is essentially 100% selective in the presence of a secondary amine in the same molecule.

5. The method of claim 1 wherein the amine containing a secondary amine terminus is an aminopropylated disecondary amine of the formula NH$_2$—CH$_2$CH$_2$CH$_2$—N(R)—R'—NH—R where R is a secondary or tertiary alkyl of 3–10 carbons and R' is ethylene or

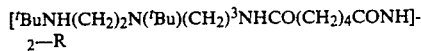

where $x$ is 1 to 3.

6. The method of claim 5 wherein the aminopropylated disecondary amine is selected from the group consisting of N-(3-aminopropyl)-N,N'-diisopropylethylenediamine (APDIPEDA) and N-(3-aminopropyl)-N,N'-di-tert-butylethylenediamine.

7. The method of claim 1 wherein the reaction takes place at a temperature of about 150° C. to about 280° C.

8. A method for the selective formation of amidoamines which comprises reacting a diacid with an aminopropylated disecondary amine of the formula NH$_2$CH$_2$CH$_2$CH$_2$N(R)—R'—NH—R at a temperature of from about 160° C. to about 270° C., where R is a secondary or tertiary alkyl of 3–10 carbons and R' is ethylene or (CH$_2$CH$_2$O)$_x$CH$_2$CH$_2$, where x is 1 to 3.

* * * * *